US009757153B2

(12) United States Patent
Jay et al.

(10) Patent No.: US 9,757,153 B2
(45) Date of Patent: Sep. 12, 2017

(54) EXTERNAL FIXATOR

(71) Applicant: WRIGHT MEDICAL TECHNOLOGY, INC., Memphis, TN (US)

(72) Inventors: Richard Jay, Philadelphia, PA (US); Joseph J. Smith, Elkins Park, PA (US); Norman G. Storer, III, Lafayette Hill, PA (US); James C. Barnitz, Schwenksville, PA (US); Michael J. Rello, Harleysville, PA (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 14/424,923

(22) PCT Filed: Sep. 6, 2013

(86) PCT No.: PCT/US2013/058369
§ 371 (c)(1),
(2) Date: Feb. 27, 2015

(87) PCT Pub. No.: WO2014/055202
PCT Pub. Date: Apr. 10, 2014

(65) Prior Publication Data
US 2015/0257788 A1 Sep. 17, 2015

Related U.S. Application Data

(60) Provisional application No. 61/697,662, filed on Sep. 6, 2012.

(51) Int. Cl.
*A61B 17/00* (2006.01)
*A61B 17/62* (2006.01)
*A61B 17/64* (2006.01)

(52) U.S. Cl.
CPC .......... *A61B 17/62* (2013.01); *A61B 17/6425* (2013.01)

(58) Field of Classification Search
CPC .. A61B 17/62; A61B 17/6425; A61B 17/6441
(Continued)

(56) References Cited

U.S. PATENT DOCUMENTS 5,540,686 A * 7/1996 Zippel ................ A61B 17/6441
606/56
5,681,309 A * 10/1997 Ross, Jr. ................ A61B 17/62
606/54
(Continued)

FOREIGN PATENT DOCUMENTS

WO 2008002992 A1 1/2008
WO WO 2008002992 A1 * 1/2008 ........... A61B 6/0421

OTHER PUBLICATIONS

International Searching Authority, PCT Office of USPTO, PCT International Search Report regarding corresponding PCT Application No. PCT/US2013/058369 issued Dec. 12, 2013, pp. 1-3.
(Continued)

*Primary Examiner* — Ellen C Hammond
*Assistant Examiner* — Stuart S Bray
(74) *Attorney, Agent, or Firm* — Duane Morris LLP

(57) ABSTRACT

An external fixator for mounting to a patient's leg or other anatomy to stabilize bones in the patient's leg or other anatomy includes a first ring including a first plurality a slots therein and a second ring including a second plurality of slots therein. A foot-plate has a generally U-shape and a third plurality of slots therein. A first strut is mounted between the first ring and the second ring. The first strut includes an upper tube, a lower tube, a first telescoping element securing the upper tube to the lower tube and first and second end fittings secured to ends of the upper and lower tubes,
(Continued)

respectively. The first end fitting secures the first strut to the first ring and the second end fitting secures the first strut to the second ring.

20 Claims, 14 Drawing Sheets

(58) Field of Classification Search
USPC .................................................. 606/56
See application file for complete search history.

(56) References Cited

U.S. PATENT DOCUMENTS

| | | | | | |
|---|---|---|---|---|---|
| 5,797,908 | A * | 8/1998 | Meyers | ............... | A61B 17/6483 606/54 |
| 5,863,292 | A * | 1/1999 | Tosic | ............... | A61B 17/62 606/56 |
| 5,885,282 | A * | 3/1999 | Szabo | ............... | A61B 17/62 606/56 |
| 5,971,984 | A * | 10/1999 | Taylor | ............... | A61B 17/62 128/898 |
| 6,017,341 | A * | 1/2000 | Windhagen | ............... | A61B 17/02 606/102 |
| 6,030,386 | A * | 2/2000 | Taylor | ............... | A61B 17/62 606/54 |
| 6,129,727 | A * | 10/2000 | Austin | ............... | A61B 17/62 606/56 |
| 6,355,037 | B1 * | 3/2002 | Crosslin | ............... | A61B 17/6425 606/54 |
| 7,749,224 | B2 * | 7/2010 | Cresina | ............... | A61B 17/6425 606/54 |
| 7,815,586 | B2 * | 10/2010 | Grant | ............... | A61F 5/0585 128/846 |
| 7,887,537 | B2 * | 2/2011 | Ferrante | ............... | A61B 17/645 24/490 |
| 7,955,333 | B2 * | 6/2011 | Yeager | ............... | A61F 5/0195 606/54 |
| 8,574,232 | B1 * | 11/2013 | Ross | ............... | A61F 5/042 606/250 |
| 8,864,763 | B2 * | 10/2014 | Murray | ............... | A61B 17/66 606/56 |
| 2003/0153910 | A1 * | 8/2003 | Janowski | ............... | A61B 17/645 606/56 |
| 2003/0181911 | A1 * | 9/2003 | Venturini | ............... | A61B 17/6466 606/56 |
| 2004/0073212 | A1 * | 4/2004 | Kim | ............... | A61B 17/62 606/56 |
| 2004/0116926 | A1 * | 6/2004 | Venturini | ............... | A61B 17/62 606/56 |
| 2004/0167518 | A1 * | 8/2004 | Estrada, Jr. | ............... | A61B 17/62 606/56 |
| 2005/0215997 | A1 * | 9/2005 | Austin | ............... | A61B 17/62 606/56 |
| 2005/0251136 | A1 * | 11/2005 | Noon | ............... | A61B 17/66 606/56 |
| 2006/0235384 | A1 * | 10/2006 | Rovesti | ............... | A61B 17/645 606/56 |
| 2007/0049930 | A1 * | 3/2007 | Hearn | ............... | A61B 17/66 606/56 |
| 2007/0055234 | A1 * | 3/2007 | McGrath | ............... | A61B 17/62 606/56 |
| 2008/0234554 | A1 * | 9/2008 | Vvedensky | ............... | A61B 17/62 600/300 |
| 2008/0269741 | A1 * | 10/2008 | Karidis | ............... | A61B 17/62 606/56 |
| 2009/0036890 | A1 * | 2/2009 | Karidis | ............... | A61B 17/62 606/56 |
| 2009/0069811 | A1 * | 3/2009 | Lindfors | ............... | A61B 90/14 606/56 |
| 2009/0177198 | A1 * | 7/2009 | Theodoros | ............... | A61B 17/66 606/56 |
| 2009/0312757 | A1 * | 12/2009 | Kehres | ............... | A61B 17/62 606/56 |
| 2009/0326532 | A1 * | 12/2009 | Schulze | ............... | A61B 17/6441 606/56 |
| 2010/0087819 | A1 * | 4/2010 | Mullaney | ............... | A61B 17/62 606/56 |
| 2010/0234844 | A1 * | 9/2010 | Edelhauser | ............... | A61B 17/62 606/56 |
| 2010/0305568 | A1 * | 12/2010 | Ross | ............... | A61B 17/62 606/56 |
| 2010/0312243 | A1 * | 12/2010 | Ross | ............... | A61B 17/62 606/56 |
| 2011/0118737 | A1 * | 5/2011 | Vasta | ............... | A61B 17/62 606/56 |
| 2011/0118738 | A1 * | 5/2011 | Vasta | ............... | A61B 17/62 606/56 |
| 2011/0208187 | A1 * | 8/2011 | Wong | ............... | A61B 17/6416 606/59 |
| 2011/0245830 | A1 * | 10/2011 | Zgonis | ............... | A61B 17/62 606/57 |
| 2011/0313418 | A1 * | 12/2011 | Nikonovas | ............... | A61B 17/62 606/56 |
| 2011/0313419 | A1 * | 12/2011 | Mullaney | ............... | A61B 17/62 606/56 |
| 2012/0029516 | A1 * | 2/2012 | Taylor | ............... | A61B 17/62 606/56 |
| 2012/0041439 | A1 * | 2/2012 | Singh | ............... | A61B 17/62 606/54 |
| 2012/0078251 | A1 * | 3/2012 | Benenati | ............... | A61B 17/6425 606/56 |
| 2012/0232554 | A1 * | 9/2012 | Shaevitz | ............... | A61B 17/171 606/56 |
| 2013/0116692 | A1 * | 5/2013 | Daluiski | ............... | A61B 17/66 606/56 |
| 2013/0123784 | A1 * | 5/2013 | Ross | ............... | A61B 17/62 606/56 |
| 2013/0204248 | A1 * | 8/2013 | Singh | ............... | A61B 17/62 606/56 |
| 2013/0253511 | A1 * | 9/2013 | Cheng | ............... | A61B 17/64 606/56 |
| 2013/0253512 | A1 * | 9/2013 | Crozet | ............... | A61B 17/62 606/56 |
| 2014/0058389 | A1 * | 2/2014 | Singh | ............... | A61B 17/66 606/56 |
| 2014/0276817 | A1 * | 9/2014 | Murray | ............... | A61B 17/62 606/56 |
| 2014/0276820 | A1 * | 9/2014 | Cresina | ............... | A61B 17/645 606/56 |
| 2015/0112339 | A1 * | 4/2015 | Lindahl | ............... | A61B 5/4595 606/56 |
| 2015/0209081 | A1 * | 7/2015 | Venturini | ............... | A61B 17/645 606/56 |
| 2015/0216564 | A1 * | 8/2015 | Salomone | ............... | A61B 17/62 606/56 |
| 2015/0257788 | A1 * | 9/2015 | Jay | ............... | A61B 17/62 606/56 |
| 2015/0272624 | A1 * | 10/2015 | Singh | ............... | A61B 17/62 606/56 |
| 2015/0305776 | A1 * | 10/2015 | Ross | ............... | A61B 17/60 606/56 |
| 2016/0000465 | A1 * | 1/2016 | Ross | ............... | A61B 90/39 606/56 |
| 2016/0022314 | A1 * | 1/2016 | Bordeaux | ............... | A61B 17/62 606/56 |
| 2016/0066956 | A1 * | 3/2016 | Siemer | ............... | A61B 17/62 606/56 |

OTHER PUBLICATIONS

International Bureau of WIPO, PCT International Preliminary Report on Patentability regarding corresponding PCT Application No. PCT/US2013/058369 issued Mar. 10, 2015, pp. 1-7.

(56) References Cited

OTHER PUBLICATIONS

Office Action issued in connection with corresponding Canadian Patent Application No. 2,883,395, dated Dec. 12, 2016, 4 pages.

\* cited by examiner

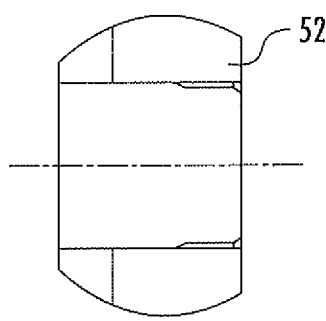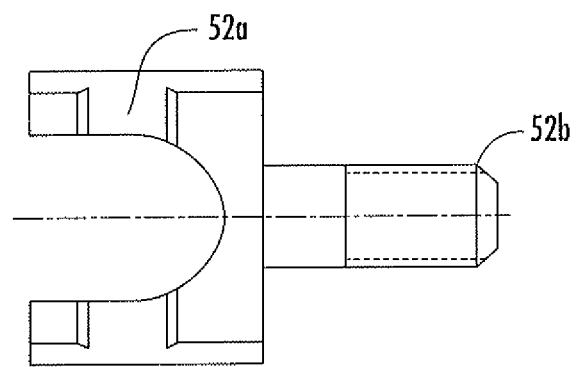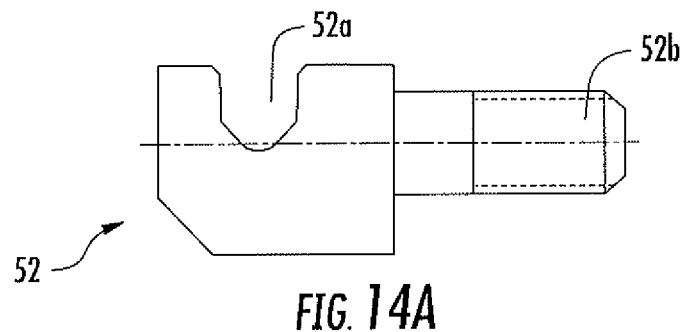
FIG. 14C  FIG. 14B
FIG. 14A

EXTERNAL FIXATOR

CROSS-REFERENCE TO RELATED APPLICATIONS

The present application is a U.S. national stage application under 35 U.S.C. §371 of International Application No. PCT/US2013/058369, filed Sep. 6, 2013, which claims priority to U.S. Provisional Patent Application No. 61/697,662, filed Sep. 6, 2012, the entireties of which are incorporated herein by reference.

BACKGROUND OF THE INVENTION

External fixation devices are typically used as a final step during complex and delicate surgeries. The external fixators are utilized to maintain the placement of bones during the healing process. The external fixator provides strength and stability to the healing bones while they regenerate, strengthen and grow.

Typical external fixation devices have been constructed of relatively heavy metallic materials that are difficult for surgeons to manipulate. Any adjustability of these prior external fixation devices typically require mechanical fasteners that require the surgeon to manipulate with both hands and/or the assistance of another surgeon or assistant to manipulate tools or to perform various other tasks to adjust the external fixator or related components. In addition, the bulky metallic structures are generally not radiolucent, thereby complicating post-operative evaluation of the regeneration and healing of the bone via imaging techniques.

Accordingly, it would be desirable to design, construct and implement an external fixator that is relatively light weight, may be both disposable and reusable, has radiolucent properties and is relatively easy to adjust and manipulate. It would also be desirable to construct an external fixator that provides flexibility of positioning along with the necessary clamping force required to maintain pretension in wires that stabilize the patient's anatomy, but has improved ease of use and a reduced cost of goods. The device is also preferably compatible with standard wires and tensioning devices. The preferred external fixator of the present invention addresses these shortcomings of existing external fixators and provides desired improvements.

BRIEF SUMMARY OF THE INVENTION

Briefly stated, the preferred external fixator includes a wire clamping assembly with a main body that incorporates an internal conical taper that interacts with a split tapered collet that clamps the wire. The angle of the taper is acute enough that the clamping action is self energizing and preferably does not require user interaction to achieve proper clamping. There is preferably a spring element that displaces the collet forward into the taper of the main body to ensure when tension is applied to the wire the clamping elements are in the proper relationship. The device is initially supplied with a disposable rear plug that spreads the collet allowing easy placement of the preferred wire clamping assembly on the wire. Once the preferred wire clamping assembly is properly placed on the wire the disposable plug is withdrawn and the device is operational. The from end of the collet has been extended beyond the main body to allow for the release of the device from the wire through the use of an auxiliary tool if the initial placement is incorrect. The geometry of the tapered elements is preferably optimized for efficient production by computer numerical controlled ("CNC") Swiss turning machines.

The preferred wire clamping assembly also incorporates features that allow for flexibility of positioning. The main body, washer and support bracket contain elements that allow for vertical and angular adjustment of the wire position relative to the external fixator frame. Once again the geometry and placement of the features are preferably optimized for efficient production by CNC Swiss turning machines.

The preferred wire clamping assembly also preferably includes a rear polymer cap that protects the patient: from the sharp end of the wire after it is cut to length. The cap has an annular snap fit that interacts with a mating feature on the rear of the main body. The geometry of the polymer cap and the snap fit feature is preferably optimized for ease of production.

BRIEF DESCRIPTION OF THE SEVERAL VIEWS OF THE DRAWINGS

The foregoing summary, as well as the following detailed description of preferred embodiments of the preferred external fixator and related method of the preferred embodiment of the present invention, will be better understood when read in conjunction with the appended drawings. For the purposes of illustrating the preferred external fixator of the present invention, there are shown in the drawings preferred embodiments. It should be understood, however, that the application is not limited to the precise arrangements and instrumentalities shown. In the drawings:

FIG. 14A is a side elevational view of a preferred fastening body of the wire clamping assembly of FIG. 10;

FIG. 14B is a top plan view of the fastening body of FIG. 14A;

FIG. 14C is a front elevational view of the fastening body of FIG. 14A;

DETAILED DESCRIPTION OF THE INVENTION

Figure 1:
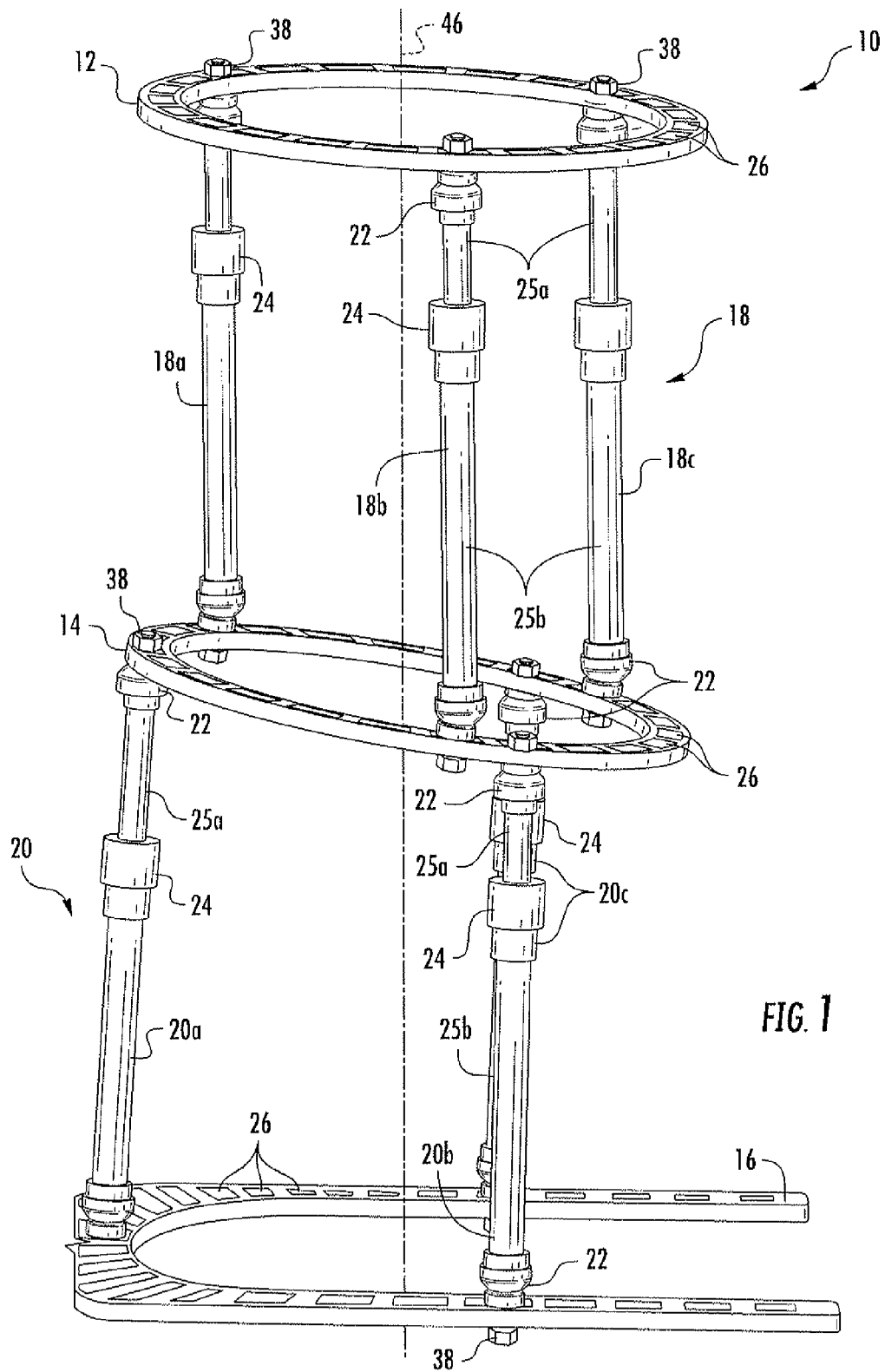
FIG. 1 is a side perspective view of an external fixator in accordance with a preferred embodiment of the present invention.
Figure 2:
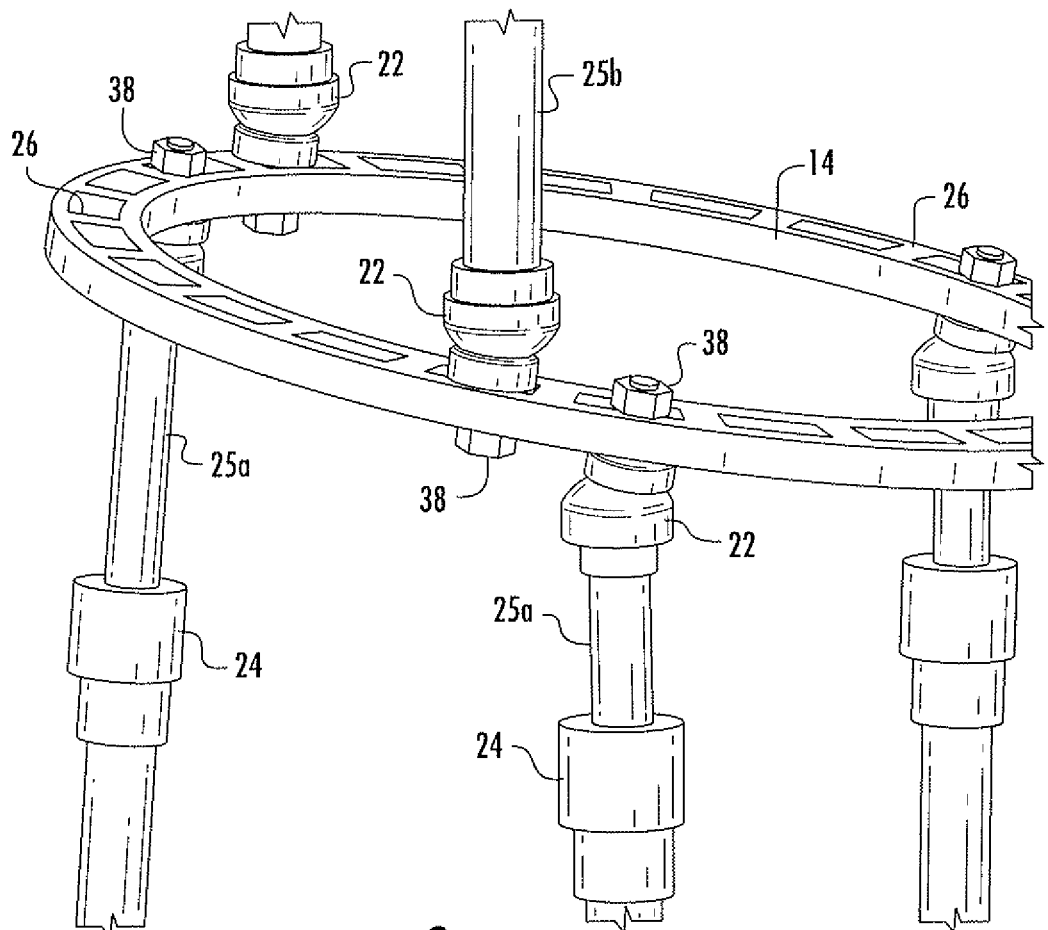
FIG. 2 is a magnified, side perspective view of a portion of the external fixator of FIG. 1.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred external fixator and/or related parts thereof. The words, "anterior", "posterior", "superior," "inferior", "lateral" and related words and/or phrases designate preferred positions, directions and/or orientations in the human body and/or a patient fitted with the preferred external fixator to which reference is made and are not meant to be limiting. The terminology includes the above-listed words, derivatives thereof and words of similar import.

Referring to FIGS. 1-4, in a preferred embodiment of an external fixator, generally designated 10, is preferably used in the treatment of acute trauma such as complex fractures, non-unions, malunions, bone defects, osteomyelitis, contracture, Charcot Reconstruction, limb lengthening procedures, deformity correction procedures and for other like conditions and/or procedures. The preferred external fixator is generally light, may be disposable or reusable and stabilizes a patient's bone(s) with the device generally positioned external to the patient's skin. The preferred external fixator 10 is preferably constructed of a significant number of radiolucent materials, is relatively light weight, has a relatively reasonable price and is disposable and/or reusable.

The preferred external fixator 10 includes a first or upper ring 12, a second or middle ring 14, a foot plate 16, a first plurality of struts 18 that secure the first ring 12 to the second ring 14 and a second plurality of struts 20 that secure the foot plate 16 to the second ring 14. These components of the preferred external fixator 10 are constructed of a selection of materials including high-quality plastic or polymeric materials, metals, such as aluminum, composite materials, such as thermosetting carbon-graphite composites or the like. The external fixator 10 of the preferred embodiment preferably permits angulation and translation adjustability in combination with light weight, strength, disposability or reusability, radiolucency and related similar features. The preferred external fixator 10 is generally easy to use with a wire or pin aiming system and allows a surgeon to reduce application time of the frame and driving of wires. The external fixator 10 may be a particularly adaptable to the Illizarov method used in orthopedic and podiatric surgical applications (leg, foot/ankle, foot).

In a preferred embodiment, the first and second rings 12, 14 have a similar construction in that they are preferably comprised of full rings with a series of slots 26 therethrough. The slots 26 are also preferably included in the foot plate 16. The slots 26 permit mounting of various elements to the first and second rings 12, 14 and foot plate 16, such as the plurality of struts 18, 20. The slots 26 preferably provide a simple means of mounting various elements and structures to the first and second rings 12, 14 and the foot plate 16 to permit adjustability of the first and second rings 12, 14 and foot plate 16 relative to each other and the patient's body. The first and second rings 12, 14 are not limited to being constructed of full rings and may be incomplete rings or have other various shapes to adapt to various anatomies of a patient's body. The preferred foot plate 16 has a generally U-shape or C-shape and includes the slots 26 throughout. The foot plate 16 is not limited to having the C-shape or the U-shape and may have nearly any shape for adaptability to a patient's body. In addition, none of the first and second rings 12, 14 nor the foot plate 16 are limited to inclusion of the slots 26 and may be constructed with other attachment means or mechanisms for attaching the first and/or second plurality of struts 18, 20 or other components thereto.

In the preferred embodiment, the first ring 12 is adjustably mounted to the second ring 14 by the first plurality of struts 18, which comprise first, second and third struts 18A, 18B, 18C in the preferred embodiment. In addition, the second ring 14 is preferably secured to the foot plate 16 by the second plurality struts 20 including a fourth strut 20A, a fifth strut 20B and a sixth strut 20C. The external fixator 10 is not limited to having the first, second and third struts 18A, 18B, 18C securing the first ring 12 to the second ring 14 nor the fourth, fifth and sixth struts 20A, 20B, 20C mounting the foot plate 16 to the second ring 14. The first and second rings 12, 14 and the foot plate 16 may be mounted to each other utilizing any number of struts 18, 20 that are able to secure the first and second rings 12, 14 and foot plate 16 relative to each other and permit adjustability of these components relative to each other under normal operating conditions of the external fixator 10.

Each of the struts 18A, 18B, 18C, 20A, 20B, 20C preferably incorporate two end fittings 22, with one at each end and a telescoping element 24 secured between the end fittings 22. The preferred end fittings 22 are designed for mounting the struts 18A, 18B, 18C, 20A, 20B, 20C to the first and/or second rings 12, 14 and the foot plate 16. The telescoping elements 24 are provided to permit a relatively simple telescopic length adjustment of the struts 18A, 18B, 18C, 20A, 20B, 20C. In combination, the end fittings 22 and telescoping elements 24 permit angular and linear adjustment of the first and second rings 12, 14 and foot plate 16 relative to each other and the patient's body in multiple axes in a relatively intuitive manner. The end fittings 22 preferably provide a relatively loose self-locking feature that is able to support at least the weight of the components of the preferred external fixator 10 to hold the external fixator 10 in certain configurations without collapsing or locking the end fittings 22 and/or telescoping elements 24 in a final locked position, as will be described in greater detail below. The preferred external fixator 10 preferably provides easy adjustment on all three planes in height, as well as compression and angular orientation.

Referring to FIGS. 3-8B, the end fittings 22 are preferably comprised of a series of nesting shell elements. The preferred shell elements allow for angular adjustment of the first and second rings 12, 14 and the foot plate 16 relative to each other in multiple axes in a very intuitive manner and only have a single attachment and locking stud. The preferred nesting shells generally provide reliable attachment and locking of the end fittings 22 in specific configurations. The preferred nesting shells assembly are also designed for efficient production by Computer Numerical Control ("CNC") machining techniques and turning machines.

Each of the struts 18, 18A, 18B, 18C, 20A, 20B, 20C includes an upper end fitting 22a and a lower end fitting 22b. In addition, each of the end fittings 22, 22a, 22b are preferably constructed of an assembly including an end plate 28, a spring element 30, a shell 32, an end plate fastener 34 and a washer 36. The end plates 28 preferably provide an attachment area or point for mounting to one end of the struts 18, 18A, 18B, 18C, 20, 20A, 20B, 20C and provide rigidity for the shell 32. The spring element 30 is preferably mounted between the end plate 28 and the end plate fastener 34 to provide partial locking of the end fittings 22 that support preliminary configuring of the preferred external fixator 10. The spring element 30 is preferably mounted within the shell 32 in an assembled configuration. The spring element 30 is preferably constructed of a compression spring or compression spring material that is able to take on the size and configuration of the spring element 30 and withstand the normal operating conditions of the spring element 30. The shell 32 preferably has an inner spherical contact surface 32a and an outer spherical contact surface 32b to provide adjustability for the end fittings 22 and locking capabilities. The end plate fastener 34 preferably includes a spherical contact surface 34a, a shaft 34b and a threaded section 34c. The spherical surface 34a of the end plate fastener 34 preferably contacts the inner spherical surface 32a of the shell 32 to provide for adjustment and locking. The shaft 34b preferably provides for attachment to the first and/or second rings 12, 14 and/or the foot plate 16. The threaded section 34c preferably engages a nut 38 for securing the end fittings 22 to the first and/or second rings 12, 14 and/or the foot plate 16. The washer 36 preferably provides a spherical contact surface 36a to engage the outer spherical surface 32b of the shell 32 and a relatively planar surface 36b that engages the first or second rings 12, 14 or the foot plate 16 in a mounted position.

Figure 3:
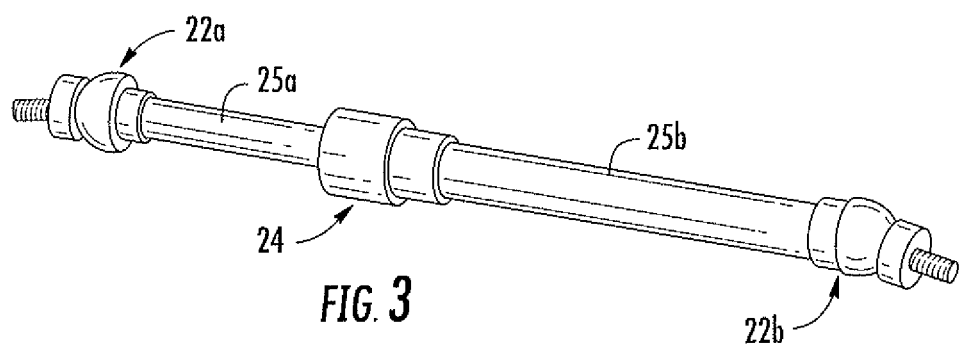
FIG. 3 is a side perspective view of a strut with end fittings on both ends for use with the preferred external fixator of FIG. 1.
Figure 4:
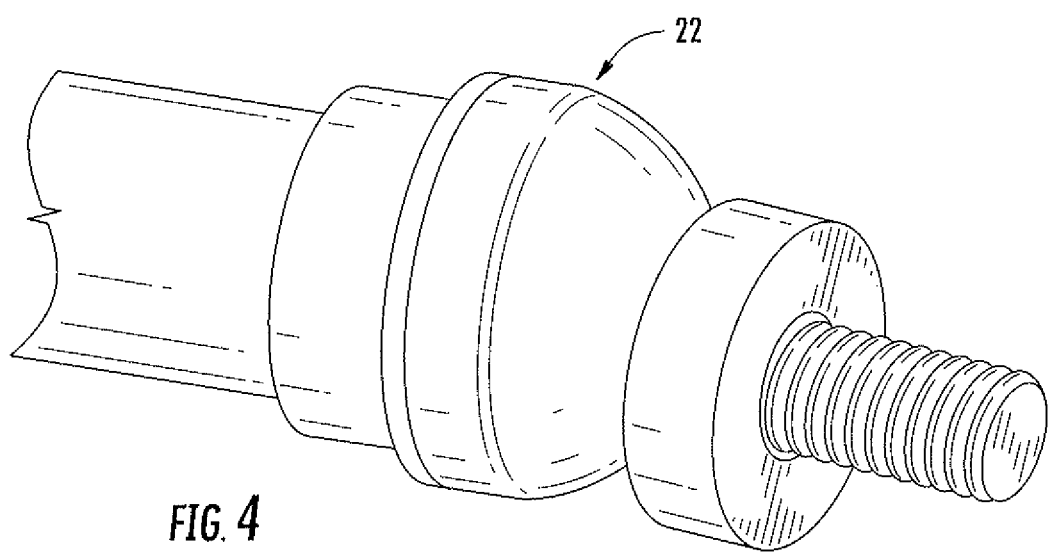
FIG. 4 is a magnified, side perspective view of one of the end fittings and an end portion of the strut of the strut and end fittings of FIG. 3.
Figure 5:
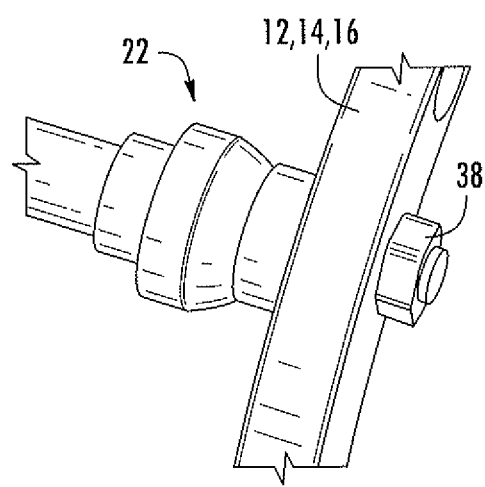
FIG. 5 is a magnified, side perspective view of a portion of a ring, and end fitting and an end of one of the struts of the external fixator of FIG. 1.
Figure 6:
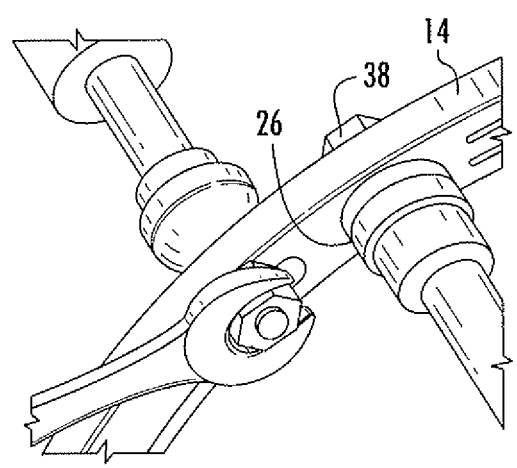
FIG. 6 is a magnified side perspective view of a portion of a second ring with a pair of end fittings mounted thereto and associated struts of the external fixator of FIG. 1.
Figure 7:
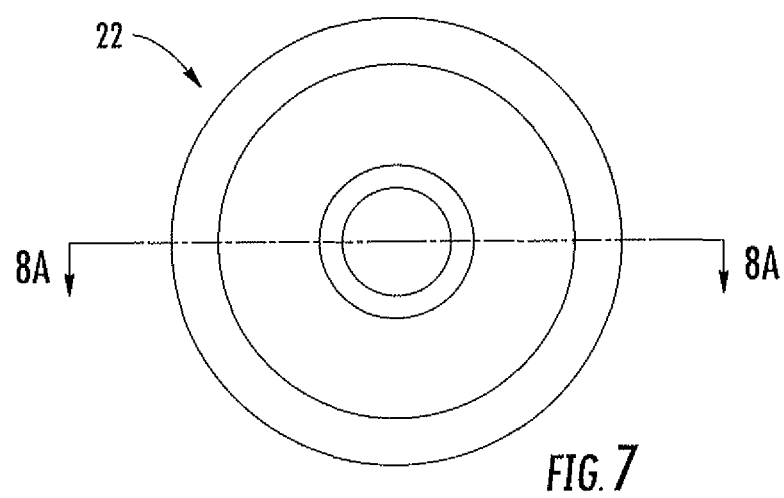
FIG. 7 is a top plan view of one of the end fittings of the external fixator of FIG. 1.
Figure 8A:
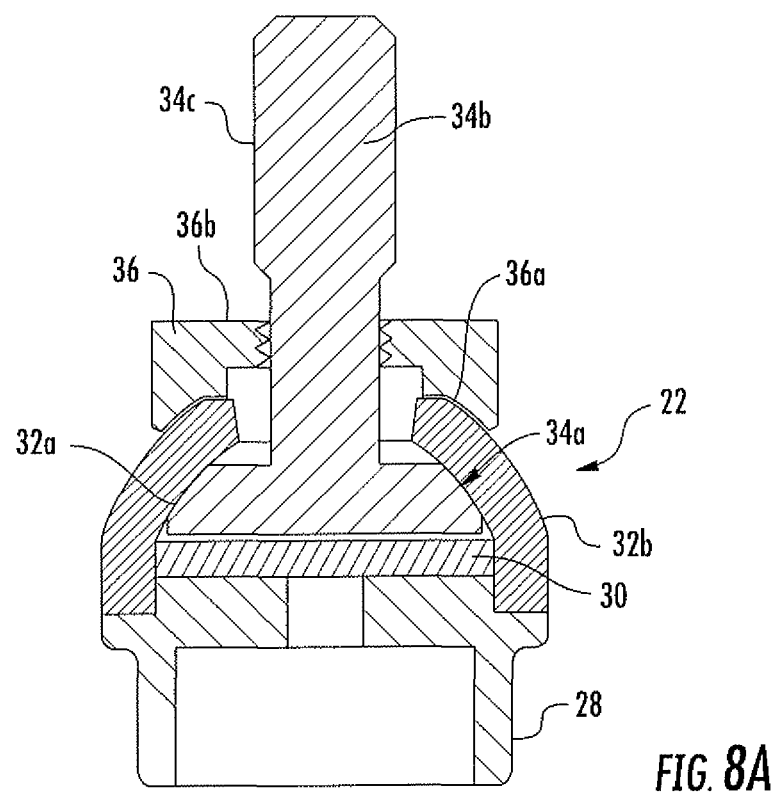
FIG. 8A is a cross-sectional view of the end fitting taken along line 8A-8A of FIG. 7.
Figure 8B:
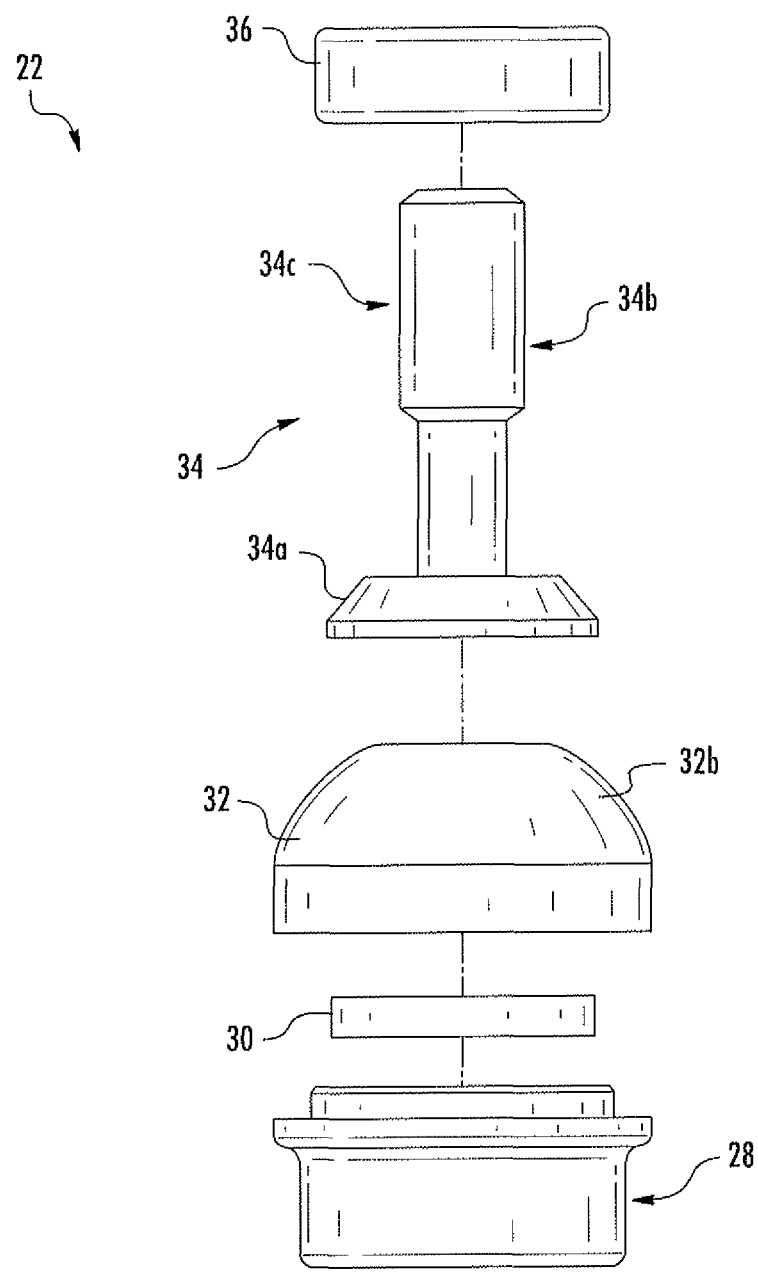
FIG. 8B is an exploded view of the end fitting of FIG. 7.
Figure 9:
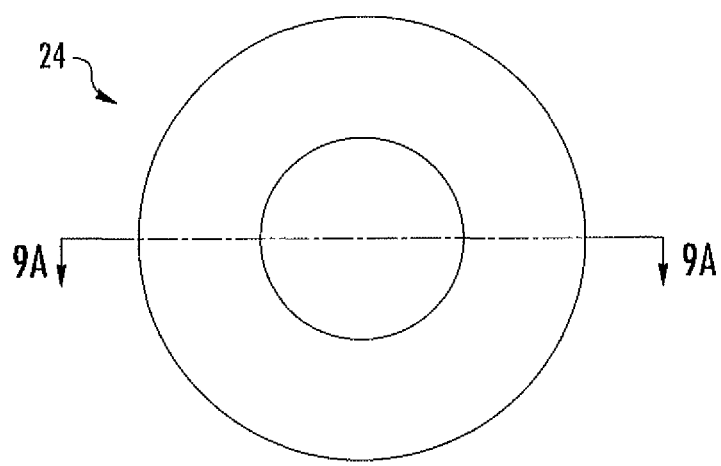
FIG. 9 is a top plan view of a telescoping fitting of the external fixator of FIG. 1.
Figure 9A:
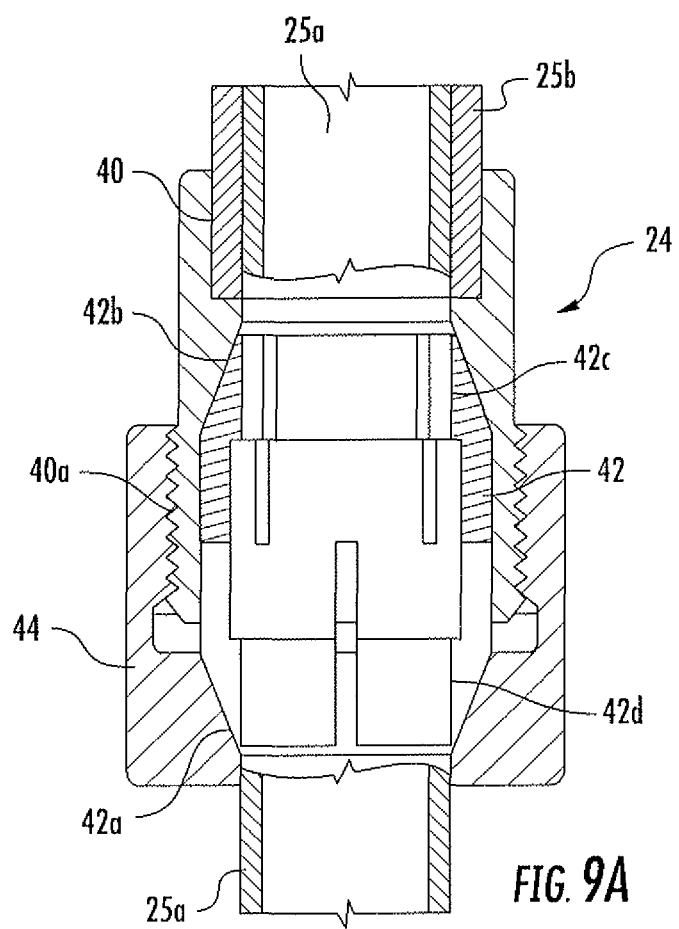
FIG. 9A is a cross-sectional view of the telescoping fitting, taken along line 9A-9A of FIG. 9, with upper and lower tubes of the preferred strut mounted thereto.
Figure 9B:
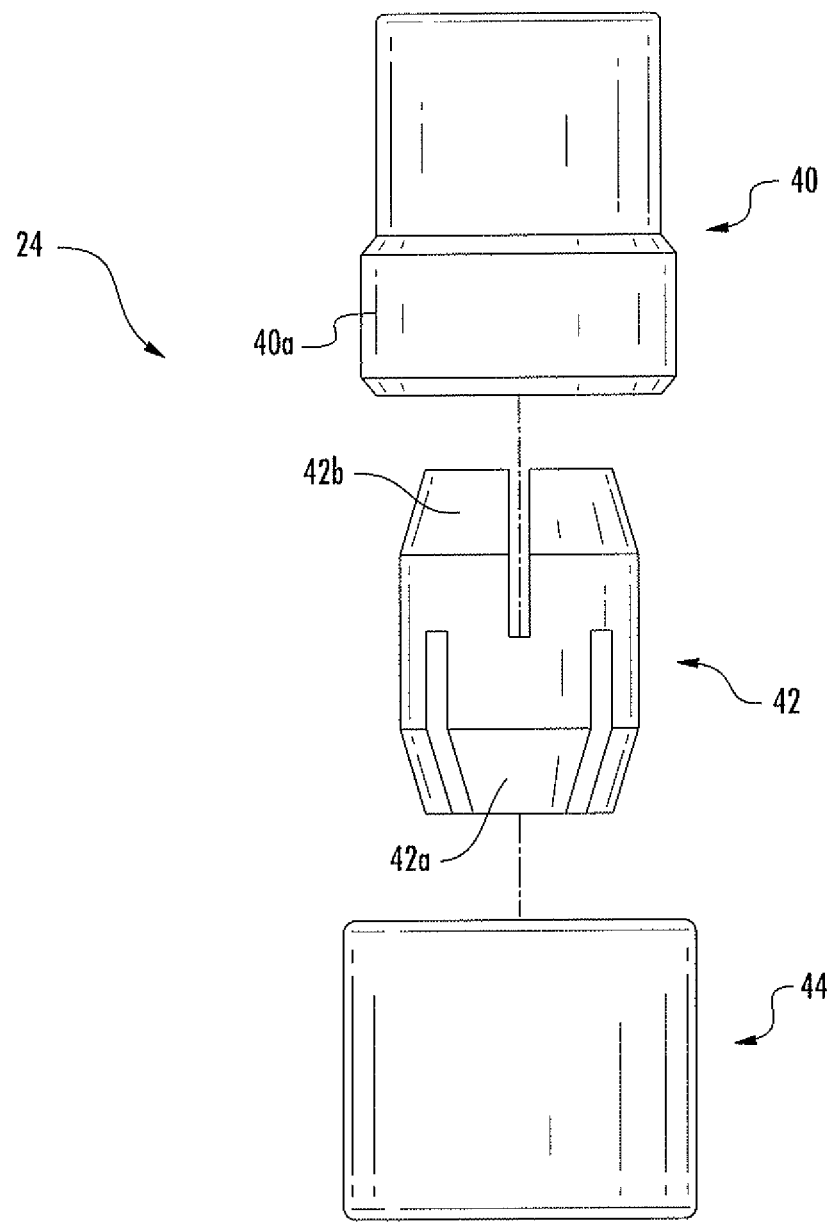
FIG. 9B is an exploded view of the telescoping fitting of FIG. 9.
Figure 10:
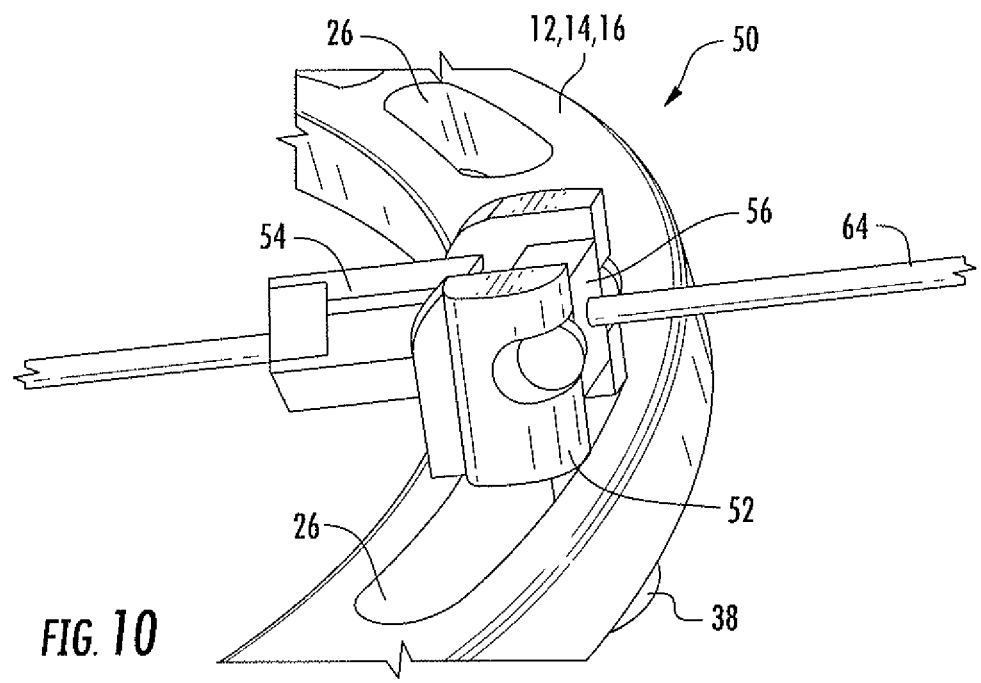
FIG. 10 is a side perspective view of a first preferred embodiment of a wire clamping assembly for use with the external fixator of FIG. 1, showing the first preferred wire clamping assembly mounted to one of the first or second rings of the preferred external fixator.
Figure 11:
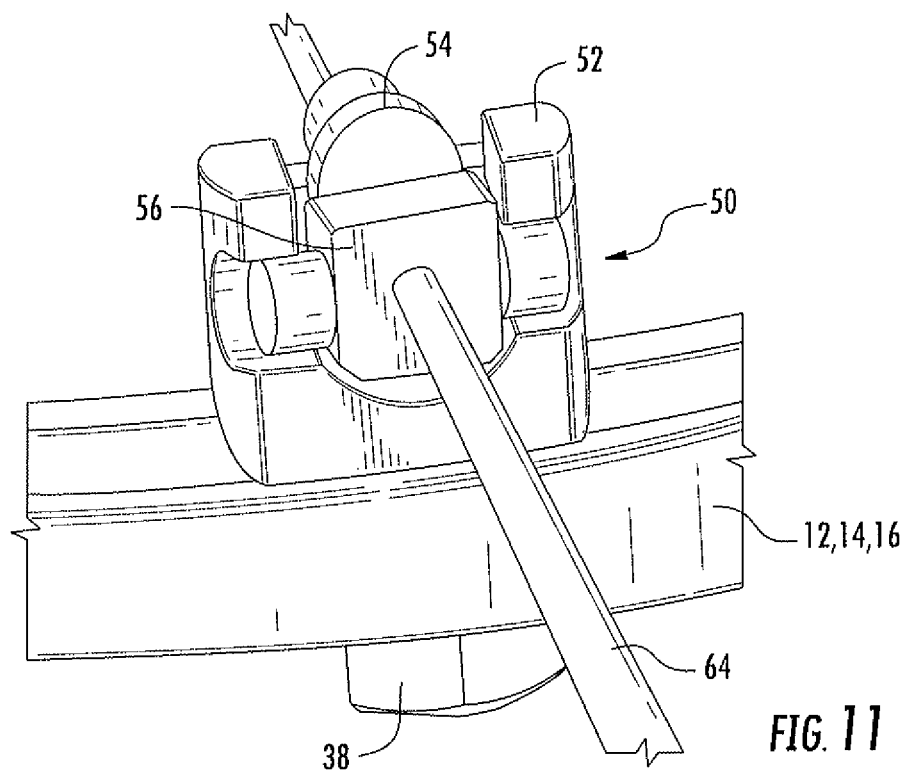
FIG. 11 is a front perspective view of the wire clamping assembly of FIG. 10 also mounted to the first or second ring of the preferred external fixator of FIG. 1.
Figure 12A:
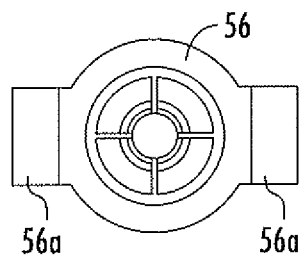
FIG. 12A is a top plan view of a preferred collet of the wire clamping assembly of FIG. 10.
Figure 12B:
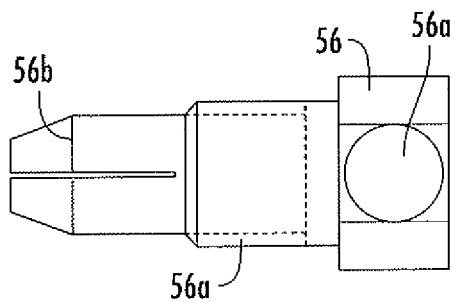
FIG. 12B is a side elevational view of the collet of FIG. 12A.
Figure 13:
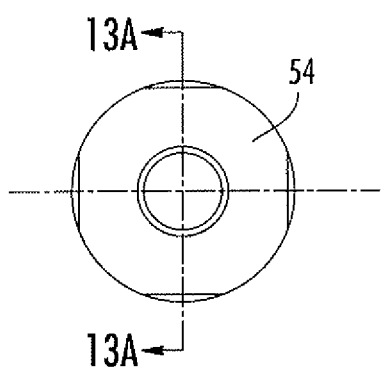
FIG. 13 is a top plan view of a main body of the wire clamping assembly of FIG. 10.
Figure 13A:
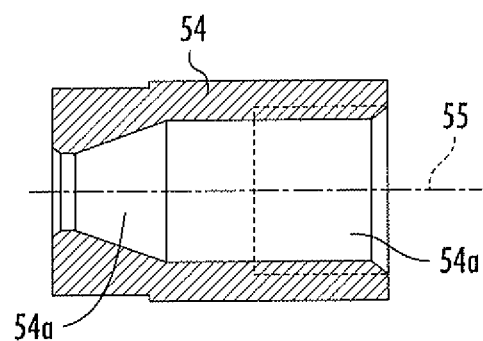
FIG. 13A is a cross-sectional view of the main body of FIG. 13, taken along line 13A-13A of FIG. 13.
Figure 15:
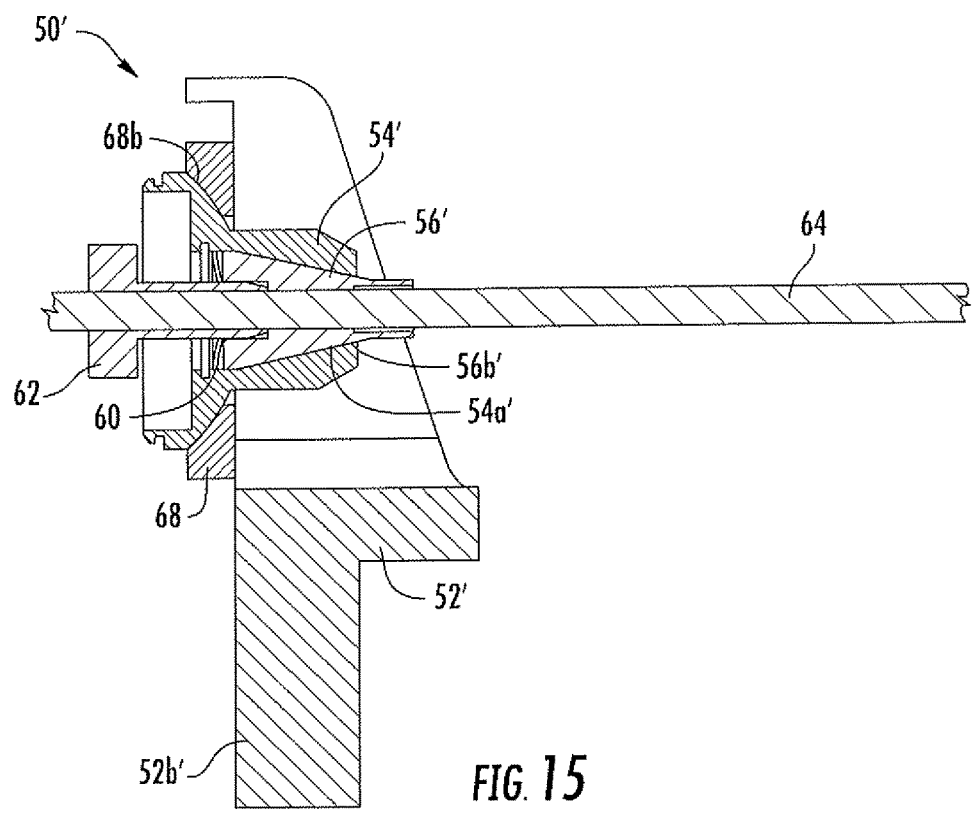
FIG. 15 is a cross-sectional view of a second preferred wire clamping assembly for use with the external fixator of FIG. 1, showing the second preferred wire clamping assembly in an expanded configuration.
Figure 16:
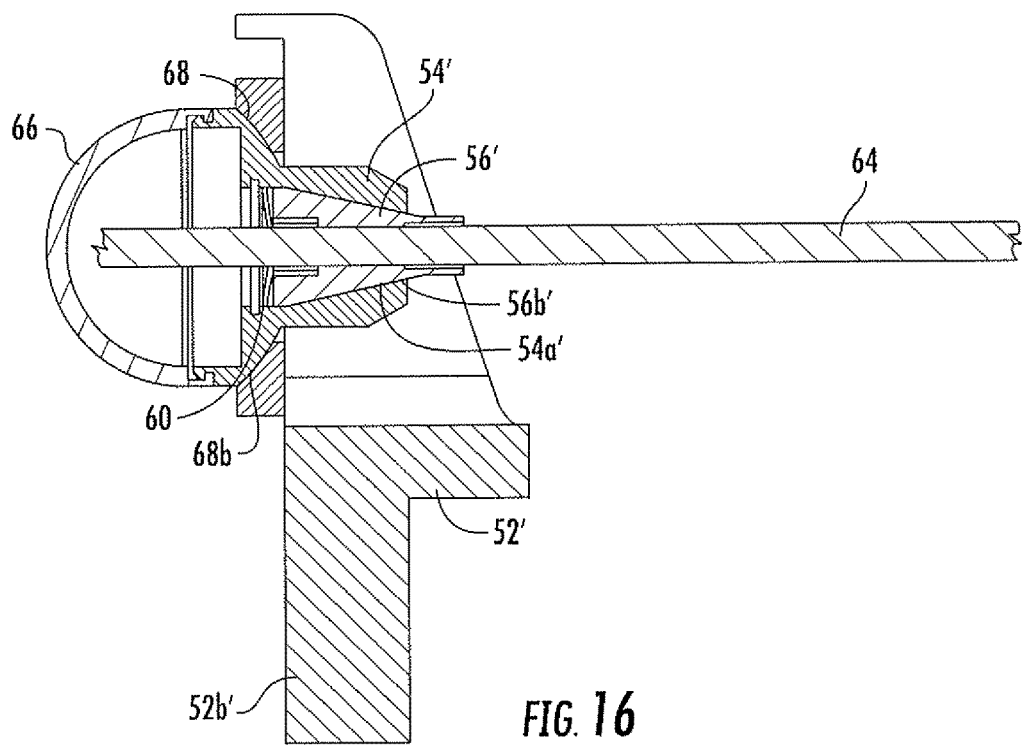
FIG. 16 is a cross-sectional view of the wire clamping assembly of FIG. 15, showing the wire clamping assembly in a clamped configuration.
Figure 17:
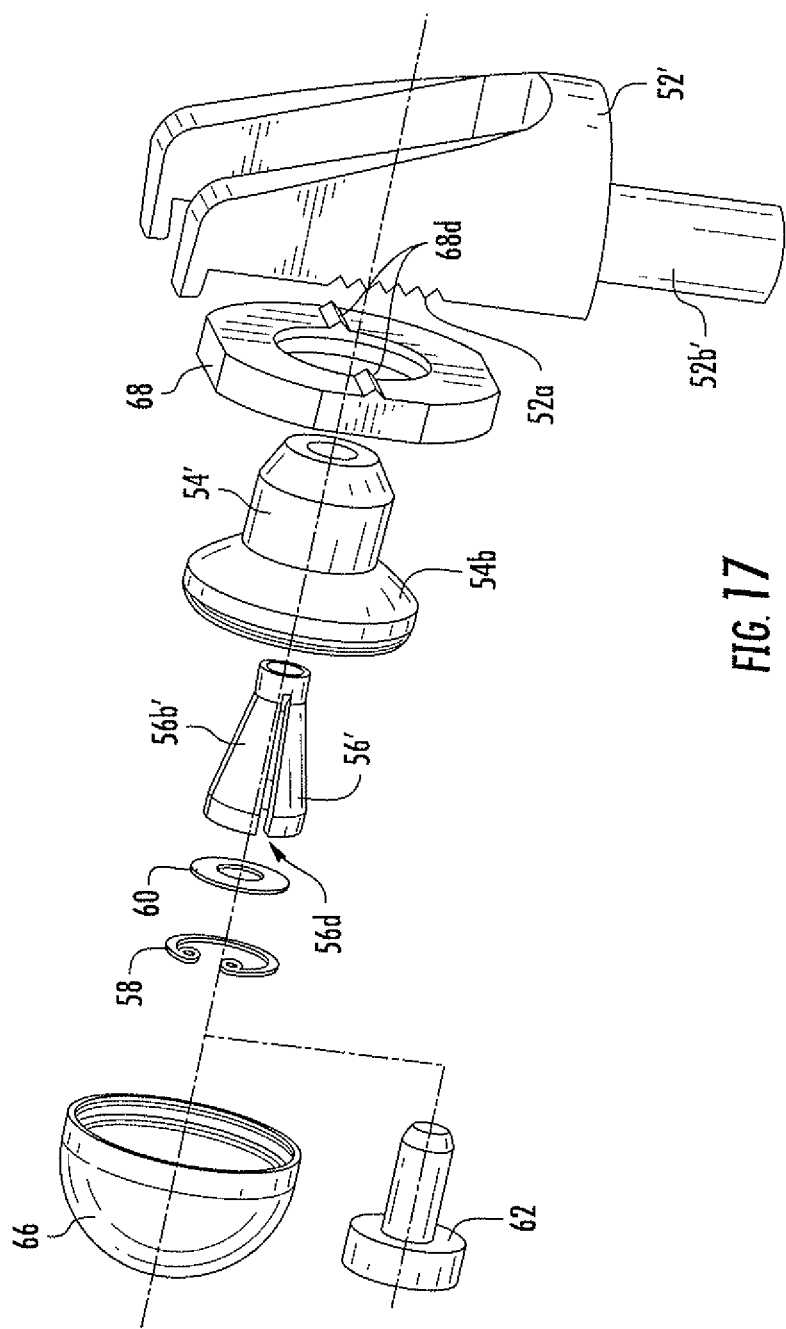
FIG. 17 is a right-side perspective, exploded view of the wire clamping assembly of FIG. 15.
Figure 18:
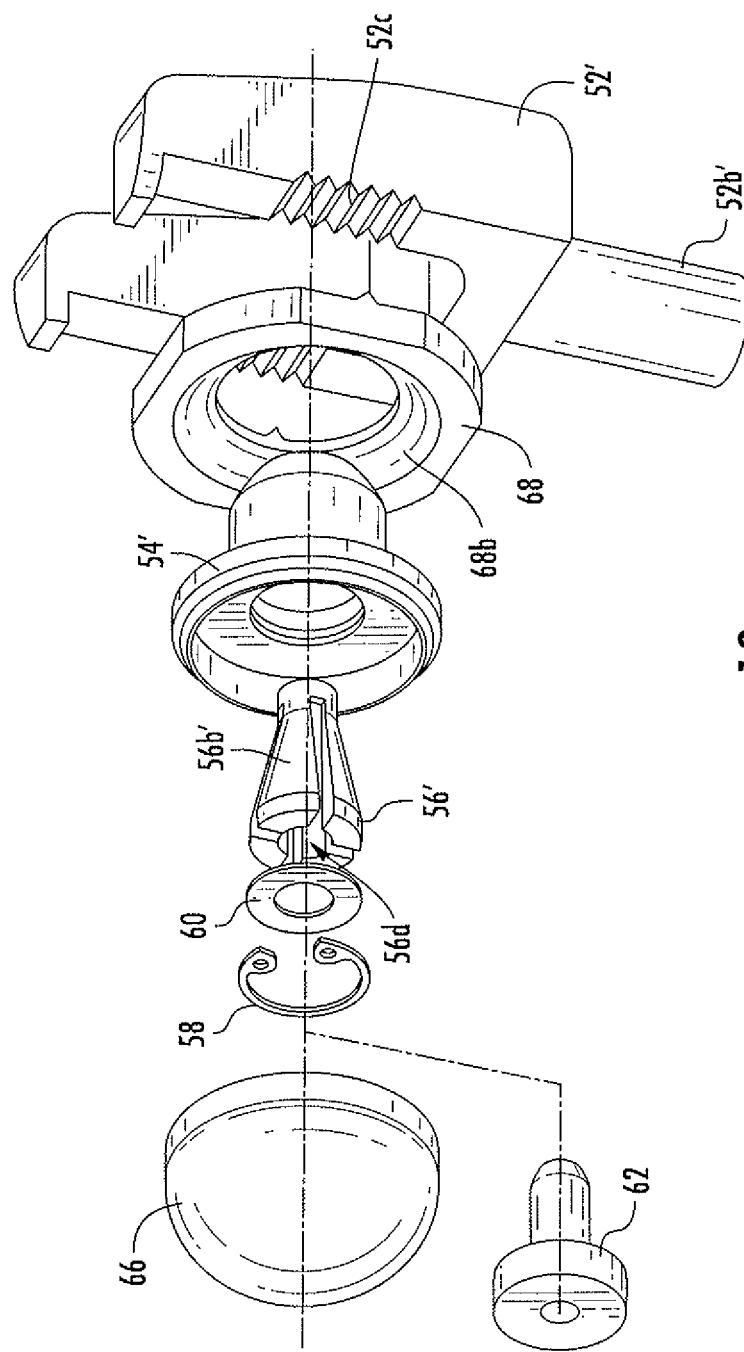
FIG. 18 is a left-side perspective, exploded view of the wire clamping assembly of FIG. 15.
Figure 19:
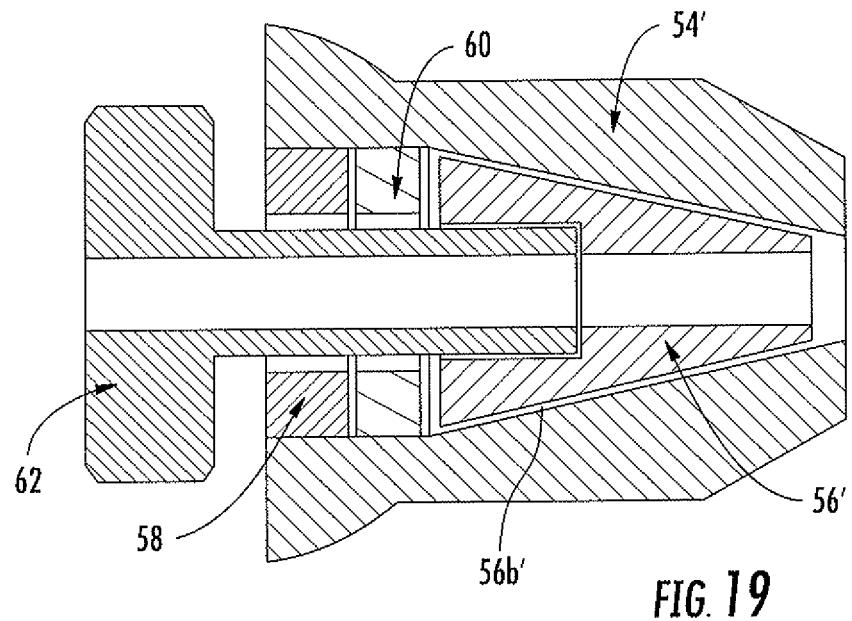
FIG. 19 is a cross-sectional view of selected elements of the wire clamping assembly of FIG. 14, showing the selected elements in the expanded configuration.
Figure 20:
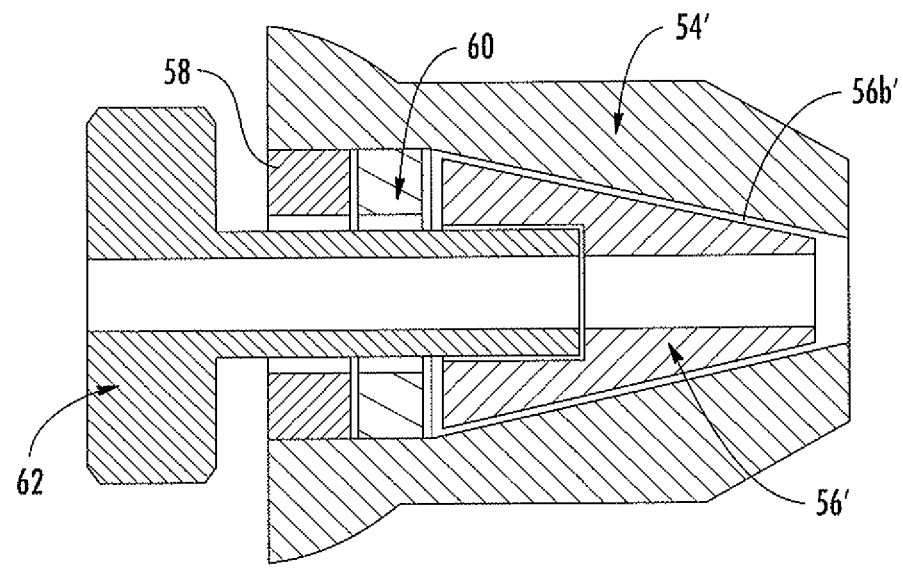
FIG. 20 is an additional cross-sectional view of the selected elements of the wire clamping assembly of FIG. 14, showing the selected elements in the expanded configuration.

Referring to FIGS. 3 and 9-9B, the struts 18, 18A, 18B, 18C, 20, 20A, 20B, 20C each preferably include one of the telescoping elements 24 mounted between an upper tube 25a that is telescopically slidable within a lower tube 25b. Accordingly, the preferred telescoping fitting 24 allows for length adjustments of the plurality of struts 18, 20. The telescoping fitting 24 is designed to provide a generally intuitive operation and a relatively rigid joint that can accommodate bending forces typically encountered during the use of the preferred external fixator 10 under normal operating conditions. The telescoping fitting 24 is configured to accommodate tolerances associated with standard commercial tubing and for efficient production by CNC machining techniques.

In the preferred embodiment, the upper and lower tubes 25a, 25b are constructed of a thermosetting epoxy and graphite composite material. More preferably, the upper and lower tubes 25a, 25b are constructed of pultruded epoxy and graphite rods or tubes. The epoxy and graphite materials provide radiolucency, relatively light weight and relatively high strength for the struts 18, 20. However, the struts 18, 20 are not limited to being constructed of graphite and epoxy composite tubes and may be constructed of nearly any material that is able to withstand the normal operating conditions of the struts 18, 20. For example, the upper and lower tubes 25a, 25b may be constructed of aluminum or other materials.

The telescoping elements 24 are preferably constructed of a lower housing 40, a double-tapered and partially flexible collet 42 and an upper housing 44. The upper housing 44 includes internal threads and the lower housing 40 includes external threads 40a that are matable with each other. The collet 42 is preferably mounted within and between the upper and lower housings 44, 40 and interacts with the upper and lower housings 44, 40 at two partially flexible or collapsible tapered surfaces 42a, 42b. In the assembled configuration, drawing the lower housing 40 toward the upper housing 44 by turning the threads causes the tapered surfaces 42a, 42b to interact with the upper and lower housings 44, 40 and to collapse onto and grip the upper tube 25a to lock the position of the upper tube 25a to the lower tube 25b. Moving the lower housing 40 away from the upper housing 44 by turning the threads in an opposite direction permits the collet 44 to flex back to a relaxed position, thereby permitting movement of the upper tube 25a relative to the lower tube 25b. Dual gripping surfaces 42c, 42d of the collet 42 are preferably spaced from each other at ends of the collet 42 for gripping the upper tube 25a. The dual gripping surfaces 42c, 42d and their spaced apart configuration permits reduction of stresses in the tubes 25a, 25b. Specifically, the spacing of the dual gripping surfaces 42c, 42d is better able to react bending forces that may be encountered by the struts 18, 20.

Wire Clamping Assembly

Referring to FIGS. 1 and 10-14C, the preferred external fixator 10 may also be utilized with a first preferred wire clamping assembly 50. The first preferred wire clamping assembly 50 is preferably mountable to the first and/or second rings 12, 14 and/or the foot plate 16 and to a wire 64. The wire 64 is secured at two locations to the rings 12, 14 and/or the foot plate 16 by a pair of the first preferred wire clamping assemblies 50 to stabilize the patient's bones or other anatomy during healing.

The first preferred wire clamping assembly 50 preferably includes a fastening body 52, a main body or nut 54 and a collet 56. The fastening body 52 includes a pair of U-shaped channels 52a and a threaded shaft 52b. The fastening body 52 is preferably removably mountable to the slots 26 using one of the nuts 38. The U-shaped channels 52a preferably face away from a center line 46 of the preferred external fixator 10 in an assembled configuration. The collet 56 of the first preferred wire clamping assembly 50 includes a pair of ears 56*a* that engage the U-shaped channels 52*a* of the fastening body 52. The main body 54 preferably includes a funnel-like or frusta-conical internal surface 54*a* that receives a funnel-like external surface 56*b* of the collet 56 to alternatively compress or release the collet 56 for clamping the wire 64. The funnel-like internal surface 54*a* of the main body 54 is preferably oriented at an approximate twenty degree) (20° angle relative to a longitudinal axis 55 of the main body 54 to provide increased clamping force for the wire clamping assembly 50. The funnel like or tapered internal surface 54*a* of the main body 54 preferably interacts with the externally tapered or funnel-like surface or end 56*b* of the collet 56 to provide clamping. The collet 56 is preferably secured to the main body 54 by external threads 56*c* on the collet 56 and internal threads 54*a* on the main body 54.

In operation, the a pair of the fastening bodies 52 are mounted opposite each other to the rings 12, 14 and/or the foot plate 16 by urging the threaded shafts 52*b* through the slots 26 on opposite sides of the rings 12, 14 and/or the foot plate 16. The fastening bodies 52 are secured to the rings 12, 14 and/or the foot plate 16 by engaging and tightening nuts 38 to the threaded shafts 52*b*. The collets 56 are positioned such that the ears 56*a* are in the U-shaped channels 52*a* with the main bodies 54 closest to the center line 46 of the preferred external fixator 10. When the wire 64 is appropriately positioned in the patient's body, the position of the wire 64 relative to the rings 12, 14 and/or the foot plate 16 is fixed by tightening the main body 54 onto the collets 56 to tightly engage the wire 64. The wire 64 may be tensioned by a tensioning tool (not shown) prior to final fixing of the wire 64. The ends of the wire 64 outward of the collets 56 are preferably cut to minimize portions of the wire 64 extending beyond the first preferred wire clamping assemblies 50 on either side of the external fixator 10.

Referring to FIGS. 15-20, a second preferred wire clamping assembly 50' includes similar features to the first preferred wire clamping assembly 50 and like reference numerals are utilized to identify like elements between the first and second preferred wire clamping assemblies 50, 50' with a prime symbol (') to specifically identify the elements of the second preferred wire clamping assembly 50'. The second preferred wire clamping assembly includes a fastening body 52', a main body 54', a collet 56', a back plate 58, a securing washer 68, a spring element 60, a plug 62 and a cap 66. The securing washer 68 includes a pair of teeth 68*a* on one side that are releasably engageable with serrations 52*c* on the fastening body 52' and a partial spherical surface 68*b* on an opposite side facing away from the fastening body 52' in an assembled configuration. The main body 54' preferably includes a partial spherical surface 54*b* that engages the partial spherical surface 68*b* of the fastening body 52' to permit pivoting adjustment of the fastening body 52' relative to the main body 54' in an assembled configuration.

The back plate 58 is preferably press fit into the main body 54' or is comprised of a snap ring that engages the main body 54' and the spring element 60 is preferably mounted between the back plate 58 and the collet 56'. The pair of teeth 68*a* preferably engage one of the sets of serrations 52*c* on the fastening body 52' and the partial spherical surface 68*b* on the securing washer 68 slidably engages the partial spherical surface 54*b* on the main body 54' in the assembled configuration. The plug 62 is preferably positioned within a cavity 56*d* at a rear of the collet 56' to maintain the collet 56' in an expanded configuration and permit movement of the wire 64 within the collet 56'. The assembly is preferably, initially placed over the wire 64 with the plug 62 positioned in the cavity 56*d*, which generally provides free sliding of the wire 64 relative to the second preferred wire clamp assembly 50'. The plug 62 is subsequently removed, thereby permitting the collet 56' to collapse on the wire 64 and at least initially secure the position of the wire 64 relative to the wire clamp assembly 50'. This initial or partial locking is caused at least partially by the spring element 60 forcing the collet 56' and its externally tapered surface 56*b* forward into the internal funnel-like or tapered surface 54*a* of the main body 54'. The partial, initial clamping force engages the wire 64 with an initial clamping force. If the wire 64 is pulled toward the center line 46 of the external fixator 10, the clamping force tends to increase on the wire 64 due to the configuration of the collet 56' and the main body 54'. The wire 64 may be more securely locked to the wire clamping assembly 50' by further urging the externally tapered surface 56*b'* of the collet 56' into the internal tapered surface 54*a'* of the main body 54' and further compressing the collet 56'. Force supplied on the wire 64 toward the center line 46 of the external fixator 10 causes additional tightening of the collet 56' because such force urges the collet 56' into the tapered surface 54*a'* of the main body 54'. The cap 66 is placed onto the end of the main body 54' to cover a sheared or cut end of the wire 64 after the wire 64 is positioned by the surgeon and cut to length to limit exposure to the cut end of the wire 64.

In operation or use of the preferred external fixator 50, the first and second rings 12, 14 are secured in a particular orientation relative to each other by mounting the first plurality of struts 18 therebetween. The orientation of the first and second rings 12, 14 relative to each other may be modified by changing the angulation of the end fittings 22 and the lengths of the individual struts 18A, 18B, 18C utilizing the telescoping elements 24. The second ring 14 is also preferably similarly secured to the foot plate 16 by the second plurality of struts 20. The patient's limb, such as a foot and leg or other anatomy are inserted, generally along the center line 46 of the external fixator 10. The partial locking of the telescoping elements 24 and end fittings 22 permit the preferred external fixator 10 to generally maintain a provisional or preliminary shape for orientation relative to the patient's anatomy.

Multiple wires 64 are then preferably mounted in the patient's anatomy to secure a desired orientation and position of the anatomy to promote healing. The wires 64 are preferably secured to the first and second rings 12, 14 and/or the foot plate 16 by either one of the first and/or second preferred wire clamping assemblies 50, 50', with pairs of wire clamping assemblies 50, 50' mounting each wire 64 at two locations to the first and second rings 12, 14 and/or the foot plate 16. The positioning of the ears 56*a* of the collet 56 in the U-shaped channels 52*a* of the fastening body 52, as well as the engagement of the fastening body 52 to the rings 12, 14 and/or plate 16 also permits angular adaptation of the orientation of the wire 64 and self-alignment when utilizing the first preferred wire assembly 50. In addition, the positioning of the pair of teeth 68*a* in the serrations 52*c* and the sliding engagement of the partial spherical surface 68*b* of the securing washer 68 with the partial spherical surface 54*b* of the main body 54' permits angular adaptation of the orientation of the wire 64 and self-alignment when utilizing the second preferred wire assembly 50'.

The design elements of the external fixator of the invention provide several advantages over the prior art in respect of ease of use and the ease and cost of manufacture. For example, the design permits single wrench tightening of strut end fittings 22 and fastening bodies 52. The flat contact surfaces of the washer 36 and the fastening body 52 that bear on a ring or foot plate have a counterbore that increases the contact radius of those surfaces. The larger contact radius provides a resisting torque due to friction that is greater than the torque due to thread friction during tightening. The spherical contact surface of the washer 36 also has a counterbore that increases the contact radius of that surface. The counterbore also increases the contact angle which increases normal forces and the associated frictional forces. The effect of both the increased contact radius and angle is a resisting torque that is greater than the torque due to thread friction. The spherical surface of the end plate fastener 34 also has been truncated near the center line. The effect is the same as the counterbore in the spherical surface of the washer.*

The design concept is to calculate the relationship between the preload created when a nut is tightened and the amount of frictional torque the nut is applying to the male threads of the mating part. As a rough estimate, it is about 40% of applied torque and may range, for example, from about 30% to about 50%, preferably from about 35% to about 45% of applied torque. The next step in the design is to develop a relationship between the preload and the resisting torque for the mating part. Once this relationship is determined, the geometry of the mating part is modified such that the resisting torque is greater than the torque applied to the threads by the nut. In the case of a flat surface, two parameters can be adjusted. These are the frictional coefficient of the surfaces in contact and the effective contact radius. For a round flat surface, the contact radius is a function of the inside diameter and the outside diameter of the mating surface. Since the outside diameters of the elements of the external fixator are limited by size and weight constraints, the inside diameter was enlarged to increase the effective contact radius and yield a resisting torque that is greater than the torque applied by the nut. The coefficient of friction could also be increased by modifying the surface but that would result in increased manufacturing costs as compared with adding a counterbore to enlarge the inside diameter. The same basic approach applies to spherical surfaces except that contact angle also needs to be taken into account because it affects the relationship between preload and resisting torque. As an example of the application of this principle, the washer 36 can have a counterbore on the flat side of 0.325 inches in diameter by 0.015 inches deep. On the spherical side, it is 0.375 inches in diameter by 0.045 inches deep. For the support bracket, it is the same as the washer.

The torque required to lock the strut and end fitting is compatible with the lower values typically seen in clinical practice, 5 Nm to 15 Nm. The use of partial spherical surfaces versus full spheres allows for the use of larger radiuses while limiting overall size and cost of the components. The larger radiuses provide a greater resisting moment for a given tightening torque. The control of the contact angles by adding counterbores or truncating the surface near the center line also provides a greater resisting moment.

The torque required to lock the telescoping element is also compatible with the lower values typically seen in clinical practice. The double tapered collet 42 provides a partially self-energizing effect in both tension and compression, reducing the required force and associated torque that is needed to lock the joint. The ability to resist both compression and tension allows the strut to be flipped end for end without affecting the performance of the telescoping element.

Another advantage is that the fastening body 52 does not need to be perfectly aligned with the axis of the wire. The spherical surfaces of the design allow both vertical and radial misalignment. The radial motion can accommodate up to 10° of misalignment without affecting performance of the wire clamp or adding additional stresses to the wire. Similar to the end fittings of the strut, the partial spherical surfaces allow the tension in the wire to provide enough resisting moment to handle any applied lateral loads to the wire.

The torque or spring force required to lock the collet in either the telescoping element or the wire clamp can be reduced by selectively applying a lubricious coating to the tapered surface of the collet or the associated housing. The reduced torque in the case of the telescoping element allows hand tightening to lock the joint for provisional placement.

The struts not only allow intuitive angular and axial motion of the rings relative to each other but also allow rotation if a wire clamping position needs to be adjusted at a resolution that is less than the spacing of the slots or holes in the ring or allows the clinician to adjust the position of a bone element that is fixed with a wire.

Manufacturing ease and cost is enhanced by the use of partial spherical surfaces versus full spheres. This allows for the use of larger radiuses. The mechanics of larger radiuses reduce the stresses in a number of components allowing for simplified designs and thinner sections. For example, the forces in the washer 36 are principally axial due to the larger radius and create compression in the washer which is easy to resist. A smaller radius would lead to greater lateral forces which would require thicker sections and a more complex design to resist. Additionally, welding or bonding the end plate 28 to the shell 32 reduces the complexity of the two parts and allows for thinner sections in both parts. The reduction in the thickness of the shell permits the use of even larger radiuses without increasing the overall dimensions of the end fitting.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description and the following claims.

We claim:

1. An external fixator for mounting to a patient's leg to stabilize bones in the patient's leg, the external fixator comprising;
a first ring including a first plurality a slots therein;
a second ring including a second plurality of slots therein; and
a first strut mounted between the first ring and the second ring, the first strut including an upper tube, a lower tube, a first telescoping element securing the upper tube to the lower tube and first and second end fittings secured to ends of the upper and lower tubes, respectively, the first end fitting securing the first strut to the first ring and the second end fitting securing the first strut to the second ring, the first end fitting configured to permit angular adjustment of the first strut relative to the first ring, the first telescoping element configured to permit modification of a distance between the first ring and the second ring, and
wherein the first end fitting comprises:
an end plate fastener secured to the first ring, the end plate fastener having a spherical contact surface, a shell attached to the upper tube of the first strut, the shell having an inner spherical surface contacting the spherical contact surface, such that the end plate fastener is rotatable within the shell, and a spring element that urges the spherical contact surface of the end plate fastener toward the inner spherical surface of the shell.

2. The external fixator of claim 1 further comprising:

a foot-plate having a generally U-shape and a third plurality of slots therein; and a second strut mounted between the second ring and the foot-plate, the second strut including an upper tube, a lower tube, a second telescoping element securing the upper tube to the lower tube and third and fourth end fittings secured to ends of the upper and lower tubes, respectively, the third end fitting securing the second strut to the second ring and the fourth end fitting securing the second strut to the foot plate.

3. The external fixator of claim 2 further comprising wire clamping assemblies, wherein, two wire clamping assemblies are affixed to each of one, two or all of the first ring, second ring or foot plate, a first wire clamping assembly being affixed to one side of a ring or foot plate and a second wire clamping assembly being affixed to an opposing side of said ring or foot plate, and a wire connected to the first wire clamping assembly and the second wire clamping assembly.

4. A method of maintaining the placement of bones during the healing process following a surgery utilizing the external fixator of claim 3 comprising orienting the first ring, second, ring and foot plate in desired positions over a patient's anatomy and securing the locations of said rings and foot plate relative to one another by affixing the first strut to the first ring and the second ring and affixing the second strut to the second ring and the foot plate;

mounting wires in desired orientations of the anatomy and affixing opposing ends of each wire to opposing sides of the first ring and/or opposing sides of the second ring and/or opposing sides of the foot plate.

5. The method of claim 4 wherein the opposing ends of at least one wire are affixed to the opposing sides of each of the first ring, the second ring and the foot plate.

6. The method of claim 4 further comprising removing the external fixator of claim 3 following healing.

7. The external fixator of claim 3 wherein more than two wire clamping assemblies are affixed to any one, two or all of the first ring, second ring and foot plate.

8. The external fixator of claim 2 wherein the first ring, the second ring and the foot plate are shaped to adapt to a patient's body.

9. The external fixator of claim 8 wherein either or both of the first ring and the second ring are not closed rings and the foot plate is optionally C-shaped.

10. The external fixator of claim 2 further comprising more than one first strut and more than one second strut.

11. The external fixator of claim 2 wherein the foot plate is a ring.

12. The external fixator of claim 1 further comprising a third ring and third strut mounted between the second ring and the third ring.

13. The external fixator of claim 12 further comprising a foot plate and a second strut mounted between the third ring and the foot plate.

14. The external fixator of claim 13 comprising more than three rings and associated struts.

15. The external fixator of claim 12 comprising more than three rings and associated struts.

16. A method of maintaining the placement of bones during the healing process following a surgery utilizing the external fixator of claim 1 comprising orienting the first ring and second ring in desired positions over a patient's anatomy and securing the locations of said rings relative to one another by affixing the first strut to the first ring and the second ring and then mounting wires in desired orientations of the anatomy and affixing the wires to the first ring and the second ring.

17. The method of claim 16 wherein each wire is affixed to opposing sides of a ring.

18. The method of claim 16 further comprising removing the external fixator of claim 1 following healing.

19. The external fixator of claim 1 further comprising more than one first strut.

20. The external fixator of claim 1, wherein the first end fitting further comprises a washer between the first ring and the upper strut, the washer having a spherical contact surface that rotatably contacts an outer spherical contact surface of the shell.

* * * * *